(12) United States Patent
Ambler et al.

(10) Patent No.: US 6,506,369 B2
(45) Date of Patent: Jan. 14, 2003

(54) TOPICAL PRODUCT WITH VISUAL INDICATOR

(75) Inventors: Philip William Ambler, Reading Berkshire (GB); Philip Norman Hole, Earley (GB); Michael J. Moloney, Brimfield, MA (US); Cheryl L. Galante, Marshfield, MA (US); Iris Davis Gersten, Rockville, MD (US); James L. Solan, Rockville, MD (US); Hermes van der Lee, Ashton, MD (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/859,073

(22) Filed: May 16, 2001

(65) Prior Publication Data

US 2002/0182233 A1 Dec. 5, 2002

(51) Int. Cl.⁷ .............................. A61K 7/42; A61K 7/32; A61K 7/34; A61K 7/38; A61K 7/46
(52) U.S. Cl. .............................. 424/65; 424/59; 424/66; 424/68; 424/400; 424/401; 424/DIG. 5; 512/1; 514/458
(58) Field of Search ................................ 424/400, 401, 424/65, 66, 68, DIG. 5, 59; 512/1; 514/458

(56) References Cited

U.S. PATENT DOCUMENTS

| | | | |
|---|---|---|---|
| D27,864 S | 11/1897 | Blackman | |
| 692,481 A | 2/1902 | Robinson | |
| 964,422 A | 7/1910 | Hood | |
| 1,669,016 A | 5/1928 | O'Neil | |
| 1,791,359 A | 2/1931 | Henriksen | |
| 2,101,540 A | 12/1937 | Gullich | |
| 2,165,420 A | 7/1939 | Siefert | |
| 2,174,779 A | 10/1939 | Delorme | |
| 2,613,185 A | 10/1952 | Marshall | |
| 2,970,083 A | 1/1961 | Bell | |
| D201,229 S | 5/1965 | Burke | |
| 3,294,692 A | 12/1966 | Kelly et al. | |
| 3,479,429 A | 11/1969 | Morshauser et al. | |
| 4,120,948 A | * 10/1978 | Shelton | |
| 4,202,879 A | * 5/1980 | Shelton | |
| 4,393,643 A | 7/1983 | Fryar et al. | |
| 4,511,552 A | 4/1985 | Cox | |
| 4,524,062 A | * 6/1985 | Laba et al. | |
| 4,578,207 A | 3/1986 | Holdt et al. | |
| 4,714,085 A | 12/1987 | Von Kleinsorgen | |
| 4,743,443 A | 5/1988 | Pisani et al. | |
| 4,786,449 A | 11/1988 | Smit | |
| 4,879,063 A | 11/1989 | Wood-Rethwill et al. | |
| 5,217,639 A | 6/1993 | Mottola | |
| D344,154 S | 2/1994 | Mottola | |
| 5,330,751 A | 7/1994 | Curtin et al. | |
| 5,417,964 A | 5/1995 | Carlson, Sr. et al. | |
| 5,538,161 A | 7/1996 | Koehler et al. | |
| 5,587,153 A | 12/1996 | Angelone, Jr. et al. | |
| 5,705,171 A | 1/1998 | Iovanni et al. | |
| 5,759,974 A | 6/1998 | Menke et al. | |
| 5,965,501 A | 10/1999 | Rattinger | |
| D423,713 S | 4/2000 | Szekely | |
| D430,346 S | 8/2000 | van der Hagen | |
| 6,096,296 A | 8/2000 | Alflen et al. | |
| D443,951 S | 6/2001 | Look | |
| D444,264 S | 6/2001 | Look | |
| D444,265 S | 6/2001 | Look | |
| D444,593 S | 7/2001 | Look | |
| D444,913 S | 7/2001 | Look | |
| D446,356 S | 8/2001 | Look | |
| D446,606 S | 8/2001 | Look | |
| D446,607 S | 8/2001 | Look | |
| D454,227 S | 3/2002 | Look | |
| D454,228 S | 3/2002 | Look | |
| D454,229 S | 3/2002 | Look | |
| D454,414 S | 3/2002 | Look | |
| D454,661 S | 3/2002 | Look | |
| D454,662 S | 3/2002 | Look | |
| D454,663 S | 3/2002 | Look | |
| D454,664 S | 3/2002 | Look | |
| D454,665 S | 3/2002 | Look | |
| D454,666 S | 3/2002 | Look | |
| D454,983 S | 3/2002 | Look | |
| D454,984 S | 3/2002 | Look | |
| D454,985 S | 3/2002 | Look | |

FOREIGN PATENT DOCUMENTS

| | | |
|---|---|---|
| DE | 199 21 183 A1 | 11/2000 |
| FR | 977194 | 3/1951 |
| GB | 2014507 A | 2/1979 |
| GB | D2081820 | 7/1999 |
| WO | WO 99/23998 | 5/1999 |
| WO | WO 00/19861 | 4/2000 |

OTHER PUBLICATIONS

The Body Shop Skin & Hair Care Products catalog holiday edition c 1995; p. 16 makeup indicated by arrows.

* cited by examiner

*Primary Examiner*—Jose' G. Dees
*Assistant Examiner*—Marina Lamm
(74) *Attorney, Agent, or Firm*—Fish & Richardson P.C.

(57) ABSTRACT

A product for application to the skin includes a container and a composition within the container including a cosmetic or therapeutic active ingredient. Sometime after first use, the application surface of the composition changes from a first visual appearance to a second visual appearance due to a change in the composition.

26 Claims, 11 Drawing Sheets

TOPICAL PRODUCT WITH VISUAL INDICATOR

TECHNICAL FIELD

This invention relates to products, for example, antiperspirants and deodorants, that are topically applied to the skin.

BACKGROUND

Antiperspirant and deodorant compositions are well known personal care products. The compositions come in a variety of forms and may be formulated, for example, into aerosols, pumps, sprays, liquids, roll-on, lotion, creams, and sticks (both hard and soft), etc.

There are various types of stick antiperspirant compositions. In one type, an antiperspirant salt is suspended in an anhydrous vehicle often including a solid water-insoluble wax. In a second type, an antiperspirant salt is dissolved in a liquid vehicle such as propylene glycol and gelled with a gelling agent such as dibenzylidene sorbitol. A third type includes an emulsion of an aqueous phase containing the antiperspirant salt and an oil phase containing, for example, a volatile silicone, fragrances, gellants, and other additives.

Stick antiperspirant products include an antiperspirant composition within a container. During use of the product, the top of the container is removed and the application surface of the composition is contacted with the underarm. Some of the composition is transferred to the skin, and the container generally also includes some mechanism for moving the composition upwards through the container to continue to provide an exposed application surface. Sometimes, when the composition has largely been consumed, the small portion of remaining stick in the composition can fall out of the container, for example, onto the floor. If the product does not fall onto the floor, the first indication that a consumer may get that the product largely has been consumed is the contact of the plastic platform used to move the composition upward through the container with the skin.

SUMMARY

Generally, the invention relates to a product for application to the skin. The product includes a container having an upper end and a non-flowable composition within the container. The composition has an application surface at the open end of the container. The application surface continuously wears away during application of the composition to the skin. The composition includes a cosmetic ingredient such as an antiperspirant salt, deodorant active ingredient, sunscreen, vitamin E, aloe, alphahydroxy acid, fragrance and/or a therapeutic ingredient such as a pharmaceutically active compound (e.g., antiinflammatory agent, hair growth promoter or inhibitor, vitamin E, a alphahydroxy acid, etc.). "Non-flowable", as used herein, means the composition does not flow out of the container when the container is inverted at room temperature.

In one aspect, the application surface has a first visual appearance prior to first use and a second visual appearance at some time after the first use caused by a change in the composition. The change can be, for example, a different color resulting from using a colorant (e.g., dye, pigment, colored bead or colored capsule) in the composition. The colorant may be used to provide a pattern (e.g., a stripe, swirl, marbling, or central core) on the application surface that either changes or becomes visible after first use of the product. The colorant may also be used to cause a change in the color of the entire application surface to provide the second visual appearance. The second visual appearance may also result from, for example, a structural change (e.g., a gap) in the composition. For purposes of the present invention, the visible appearance of a platform supporting the lower end of the composition is not considered a change in the composition and does not constitute a second visual appearance of the application surface hereunder.

In some preferred embodiments, the second visual appearance occurs when the end is near, i.e., when the composition has diminished in height by at least 70% and, preferably, at least 80%. As a result, the user will know when to have a replacement product available and can discard the product before, for example, the remaining composition in the container is dislodged from the container.

In some preferred embodiments, the composition includes a stripe extending across the application surface prior to first use. The stripe has a different color or opacity than the adjacent application surface. The stripe or the adjacent surface, for example, may be optically clear. The stripe may extend, for example, downwards from the application surface prior to first use of the product but end between 5% and 20% above the lower end of the composition.

In a second aspect, the product also includes a platform within the container. Typically, the platform is threadedly engaged with a threaded shaft such that when the shaft is rotated, for example by rotating a turnbuckle or like component positioned at the bottom of the product, the platform moves towards the open end of the container, thereby pushing out the composition. The composition has an upper portion and a lower portion and the lower portion has a different composition than the upper portion. When the lower portion becomes exposed at the open end of the container, it provides a different visual appearance on the application surface than the upper potion.

In a third aspect, the product includes a usage indicator that provides a visual indication that a predetermined portion of the composition has been consumed.

In a fourth aspect, the application surface includes a stripe extending downwardly prior to first use. The composition also includes a thin line parallel to the stripe extending upwards from the end of the composition.

"Different color", as used herein, includes different shades of a color. White and black are considered colors. A change in pearlescence is considered a different color.

"Within the container", as used herein, means that at least part of the composition is within the container; for example, when the upper end of the composition including the application surface extends above the container the composition still is considered "within the container".

Other aspects of the invention include applying the antiperspirant and/or deodorant product to the underarm in an amount effective to reduce perspiration and/or malodor and to methods of making the products.

Other features and advantages of the invention will be apparent from the description of the embodiment thereof, and from the claims.

DESCRIPTION OF DRAWINGS

FIGS. 3a–3e are side views of a method that can be used to manufacture the antiperspirant product in FIG. 1a;

DETAILED DESCRIPTION

Figure 1A:
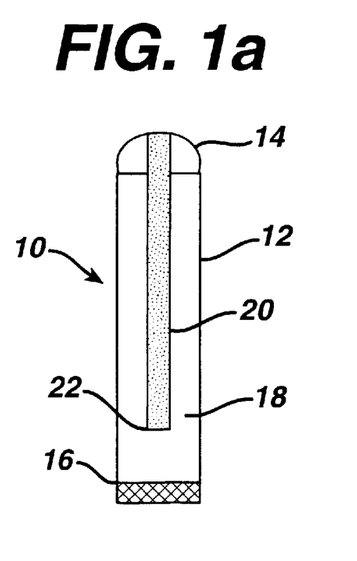
FIGS. 1a–1e are side views of an antiperspirant product including a stripe.
Figure 1B:
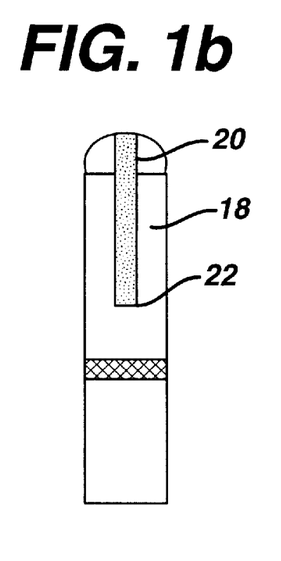
Figure 1C:
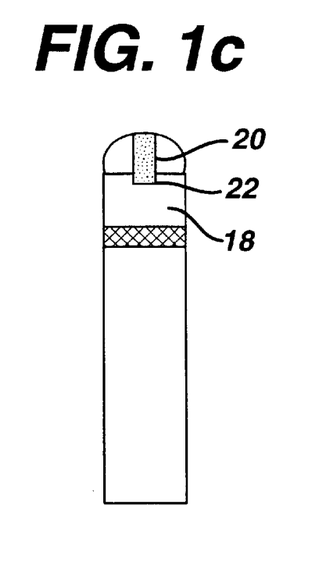
Figure 1D:
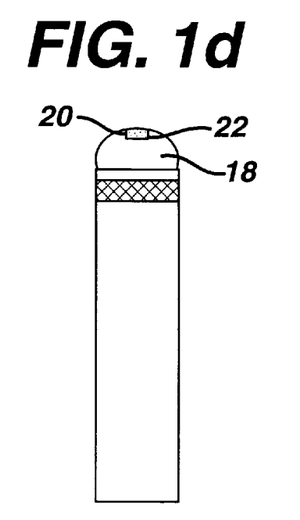
Figure 1E:
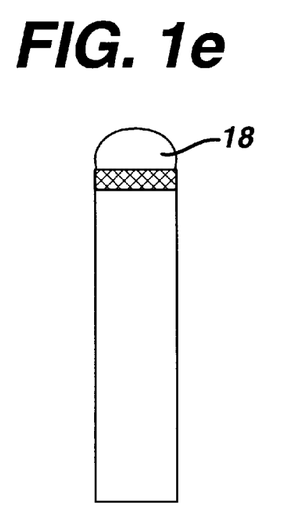
Figure 2A:
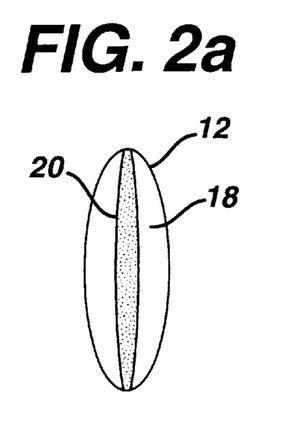
FIGS. 2a–2e are top views of the antiperspirant product in FIGS. 1a–1e, respectively.
Figure 2B:
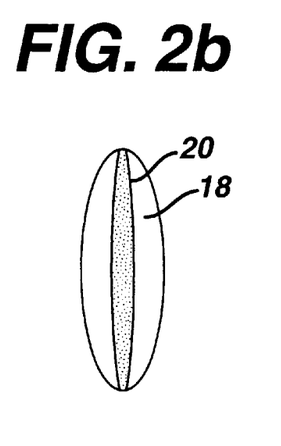
Figure 2C:
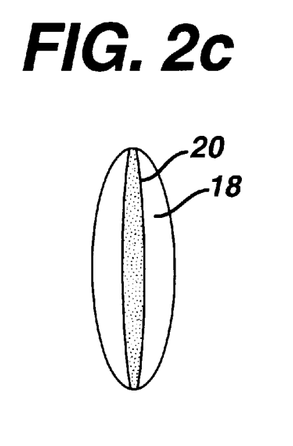
Figure 2D:
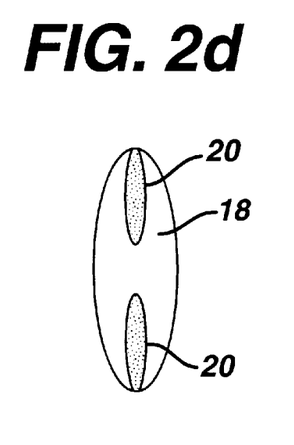
Figure 2E:
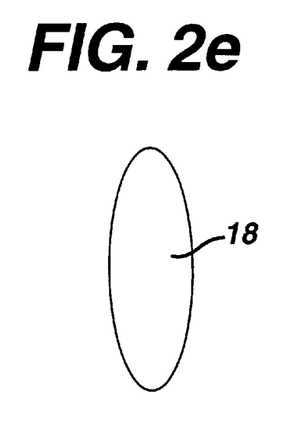
Figure 3A:
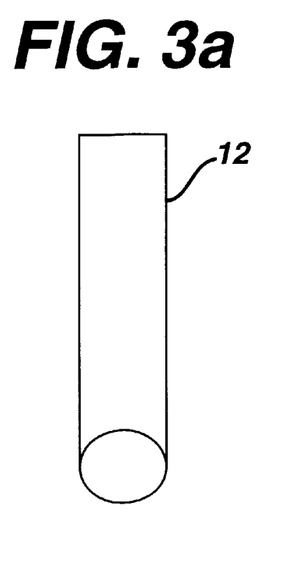
Figure 3B:
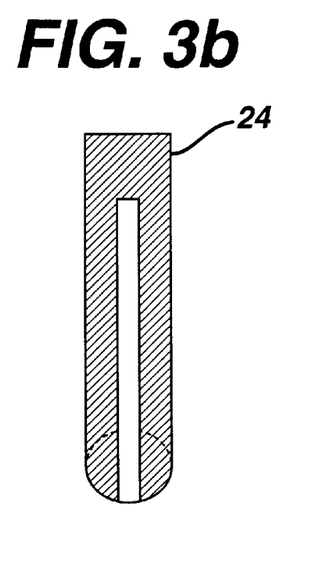
Figure 3C:
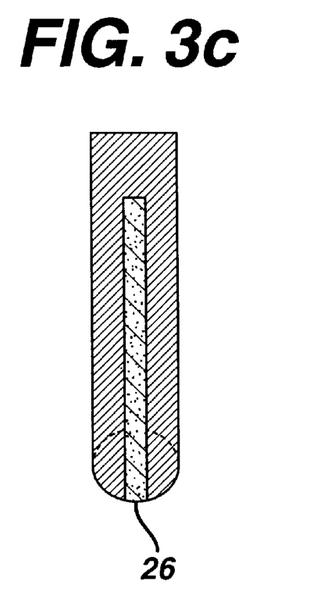
Figure 3D:
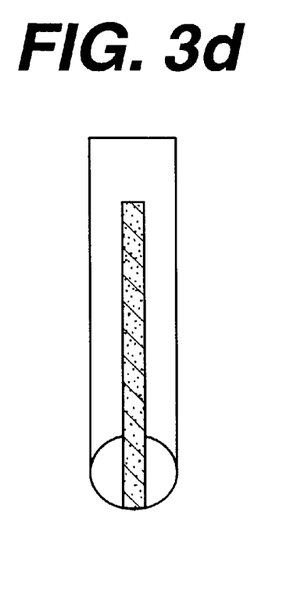
Figure 3E:
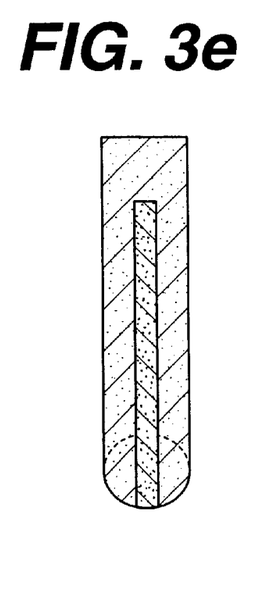

Referring to FIGS. 1a and 2a, prior to first use product 10, which may be an antiperspirant or deodorant product, includes a container 12 and a composition within the container having domed application surface 14 and lower end 16. The bottom of the container includes a platform 17 for advancing the composition upwards through the container. The composition includes portion 18 and striped portion 20 having a width, for example, of at least 0.1 inch and preferably between 0.2 inch and 0.5 inch. In product 10 striped portion 20 has a width of 0.25 inch. Striped portion 20 extends about 90% of the distance from application surface 14 towards lower end 16. Portions 18 and 20 have different compositions and portion 20 has a different color than portion 18. For example, portion 20 may be dark blue, light blue, dark green, or light green, and portion 18 may be white or vice versa.

Application surface 14 alternatively can be flat.

Referring to FIGS. 1b–1e and 2b–2e, as product 10 is used the composition is consumed. Bottom end 22 of striped portion 20 moves closer to the newly established application surface. Eventually, bottom end 22 reaches a newly established application surface (see FIGS. 1d and 2d), and the application surface visually changes in appearance (see FIG. 2d) and provides the user with a visual indication that the product 10 has largely been consumed.

Other multiple portion antiperspirant and/or deodorant compositions are described and illustrated in U.S. Ser. No. 09/784,488, filed Feb. 15, 2001, which is owned by the same owner as the present application and is hereby incorporated by reference.

One or both of portions 18 and 20 of the composition discussed above may include an antiperspirant or a deodorant active. The antiperspirant or deodorant active may either be dissolved or suspended in a dermatologically acceptable vehicle. The vehicle may typically include a volatile silicone or a polyhydric alcohol. Typically the vehicle will also include a gelling or thickening agent, such as, for example, a high melting point wax or dibenzylidene sorbitol.

The preferred antiperspirant salts are aluminum salts and aluminum zirconium salts. Preferred aluminum salts are those having the general formula $Al_2(OH)_{6-a}X_a$ wherein X is Cl, Br, I, or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X in Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{4-pb}Y_b$ wherein Y is Cl, Br, I, $NO_3$, or $SO_4$, b is about 0.8 to 4, and p is the valence of Y. The zirconium salts also generally have some water of hydration associated with them, typically on the order of 1 to 7 moles per mole of salt. Preferably the zirconium salt is zirconium hydroxychloride of the formula $ZrO(OH)_{4-b}Cl_b$ wherein b is about 0.8 to 4, preferably about 1.0 to about 4. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "AZCH" herein. Generally, the aluminum-zirconium antiperspirant salts also contain a neutral amino acid such as glycine, typically in an amount to provide a Zr:Gly ratio of about 1:1 to 4:1.

The preferred ACH and AZCH salts are of the enhanced efficacy type. By "enhanced efficacy salt" is meant an antiperspirant salt which, when reconstituted as a 10% aqueous solution, produces an HPLC chromatogram (as described, for example, in U.S. Pat. No. 5,330,751, which is incorporated herein by reference) wherein at least 50%, preferably at least 70%, most preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Particularly preferred, for example, are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "EACH" herein. Enhanced efficacy aluminum-zirconium chlorohydrate is referred to as "EAZCH" herein.

An alternative enhanced efficacy antiperspirant salt are those described in U.S. Ser. No. 09/696,271, filed on Oct. 25, 2000, which has been assigned to the same assignee as the present application and is hereby incorporated by reference. Examples of these salts are aluminum-zirconium tetrachlorohydrate or aluminum-zirconium octochlorohydrate with an HPLC peak 5 area content of at least 45%. These enhanced efficacy salts will be referred to as "$E^5AZCH$" herein.

In this application, weight percent (USP) of antiperspirant salt is calculated as anhydrous weight percent in accordance with the U.S.P. method. This calculation excludes any bound water and glycine. For aluminum chlorohydrate and aluminum-zirconium chlorohydrate, the calculation is as follows:

$\%ACH = \%Al[26.98x+17.01(3x-1)+35.45]/26.98x$ where x=Al/Cl ratio;

$\%AZCH = \%Al\{26.98y+92.97+17.01[3y+4-(y+1)/z]+35.45(y+1)/z\}/26.98y$ where y=Al/Zr ratio and z=metal/Cl ratio.

For reference purposes, calculation of antiperspirant salt weight percent in accordance with the U.S.P. method compares to the previously used standard industry method is as follows: 50% ACH (std.) approximately=40.8% (USP); 50% AZCH (std) approximately=38.5% USP.

A portion or both portions of the antiperspirant composition includes the antiperspirant salt in a perspiration reducing effective amount (typically at a concentration of about 3% to about 25% USP active, more typically about 8% to about 22% USP active).

The anhydrous, hydrophobic vehicle comprises about 60% to 95%, preferably about 70% to 90%, of a portion or the portions of the antiperspirant composition. The vehicle generally includes one or more high melting components that melt at 70° C. or higher and/or a volatile silicone.

The high melting components may include any material suitable for use in an antiperspirant stick which melts at a temperature of about 70° C. or higher. Typical of such materials are the high melting point waxes. These include beeswax, spermaceti, carnauba, bayberry, candelilla, montan, ozokerite, ceresin, and paraffin waxes, semimicrocrystalline and microcrystalline waxes, hydrogenated jojoba oil, and hydrogenated castor oil (castor wax). The preferred wax is hydrogenated castor oil. Other suitable high melting components include various types of high melting gelling agents such as polyethylene-vinyl acetate copolymers, polyethylene homopolymers, 12-hydroxystearic acid, and substituted and unsubstituted dibenzylidene alditols. Typically, the high melting components comprise about 1 to 25%, preferably about 2 to 15%, of the composition.

Volatile silicones include the cyclic polydimethylsiloxanes, also known as cyclomethicones, which have from about 3 to about 6 silicon atoms, and the linear polydimethylsiloxanes, also known as dimethicones, which have from about 2 to about 9 silicon atoms. The linear volatile silicones generally have viscosities of less than about 5 centistokes at 25° C. while the cyclic volatile silicones have viscosities under 10 centistokes; an example is DC 200, which is available from Dow Coming Corp. "Volatile" means that the material has a measurable vapor pressure at room temperature. Cyclomethicones include DC 245, DC 344, and DC 345, all of which are also available from Dow Coming Corporation. Volatile silicones are described further in U.S. Ser. No. 09/672,350, filed Sep. 28, 2000, which is assigned to the same assignee as the present application and is hereby incorporated by reference.

Other components may include, for example, non-volatile silicones, polyhydric alcohols having 3–6 carbon atoms and 2–6 hydroxy groups, fatty alcohols having from 12 to 24 carbon atoms, fatty alcohol esters, fatty acid esters, fatty amides, non-volatile paraffinic hydrocarbons, polyethylene glycols, polypropylene glycols, polyethylene and/or polypropylene glycol ethers of C4–20 alcohols, polyethylene and/or polypropylene glycol esters of fatty acids, and mixtures thereof. The term "fatty" is intended to include hydrocarbon chains of about 8 to 30 carbon atoms, preferably about 12 to 18 carbon atoms.

Non-volatile silicones include polyalkylsiloxanes, polyalkylaryl siloxanes, and polyethersiloxanes with viscosities of about 5 to about 100,000 centistokes at 25° C., polymethylphenylsiloxanes with viscosities of about 15 to about 65 centistokes, and polyoxyalkylene ether dimethylsiloxane copolymers with viscosities of about 1200 to about 1500 centistokes.

Useful polyhydric alcohols include propylene glycol, butylene glycol, dipropylene glycol and hexylene glycol. Fatty alcohols include stearyl alcohol, cetyl alcohol, myristyl alcohol, oleyl alcohol and lauryl alcohol. Fatty alcohol esters include C12–15 alcohols benzoate, myristyl lactate, cetyl acetate, and myristyl octanoate. Fatty acid esters include isopropyl palmitate, myristyl myristate, and glyceryl monostearate. Fatty amides include stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. A preferred material is hydrogenated polyisobutene with about 24 carbon atoms. Suitable polyethylene glycols and polypropylene glycols will typically have molecular weights of about 500 to 6000, such as PEG-10, PEG-40, PEG-150 and PPG-20, often added as rheology modifiers to alter product appearance or sensory attributes.

Polyethylene and/or polypropylene glycol ethers of C4–20 alcohols include PPG-10 Butanediol, PPG-14 Butyl Ether, PPG-5-Buteth-7, PPG-3-Isostearth-9, PPG-3-Myreth-3, Oleth-10, and Steareth-20. Polyethylene and/or polypropylene glycol esters of fatty acids include PEG-8 Distearate, PEG-10 Dioleate, and PPG-26 Oleate. These are generally added to give emollient properties.

The above list of materials is by way of example only and is not intended to be a comprehensive list of all potential antiperspirant stick components. Other low melting waxes, non-volatile emollients and suitable components are readily identifiable to those skilled in the art. Of course, other ingredients such as colloidal silicas, particulate polyolefins, talcum materials, fragrances, colorants and preservatives may also be included as desired. For example, the composition may include up to about 10% fragrance or about 2% colorant by weight.

Deodorant active ingredients may also be included as desired. A suitable deodorant active is any agent that inhibits, suppresses, masks or neutralizes malodor. These may include (1) antimicrobial or bactericidal agents which kill the bacteria responsible for malodor production, (2) agents which inhibit or suppress or interfere with the bacterial enzymatic pathway that produces malodor, and (3) agents which mask or absorb or neutralize malodor. Fragrances are not considered deodorant active ingredients within the meaning of this application. Examples of deodorant actives include triclosan, triclocarban, usnic acid salts, zinc phenolsulfonate, b-chloro-D-alanine, D-cycloserine, aminooxyacetic acid, cyclodextrin, sodium bicarbonate. The composition generally may comprise, by weight, about 0.01% to about 10%, preferably about 0.1% to about 6%, deodorant active.

One or both of the portions in the antiperspirant products discussed previously may include the antiperspirant salt dissolved in a polyhydric alcohol liquid carrier like propylene glycol and gelled with a gelling agent such as dibenzylidene sorbitol. This is a preferred approach to providing a product in which one or both portions are clear. Compositions of this type are described in U.S. Pat. No. 5,705,171, which is incorporated by reference herein. A preferred composition as discussed in that patent, includes about 40% to about 95% of the liquid vehicle, about 0.1% to about 5% of the gelling agent, and about 0.5% to about 25% of the antiperspirant salt. About 0.05% to about 3% of a chelating agent may also be included to improve odor and clarity.

The preferred liquid vehicles include those discussed above and in particular the polyhydric alcohols comprising 3–6 carbon atoms and 2–6 hydroxyl groups.

The preferred gelling agents for polyhydric alcohol vehicles are dibenzylidene alditols. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(meta-chlorobenzylidene) sorbitol. The preferred gelling agent is dibenzylidene sorbitol (DBS).

The composition may also include one or more of other ingredients discussed previously.

One or both of the portions of the composition may be in the form of a water-in-oil emulsion comprised of an aqueous phase including the antiperspirant salt and an oil phase including a volatile silicone. This is an alternative approach for providing a product in which one or both portions are clear. Clarity is achieved by matching the refractive index of the water phase with the refractive index of the oil phase. Compositions of this type are described in U.S. Pat. No. 5,587,153, which is incorporated by reference herein.

The water phase may include water and other polar species such as the mono- and polyhydric alcohols including discussed previously. The water phase may comprise, for example, between about 70% and about 90% of the composition by weight.

The oil phase may include one or more of the volatile silicones and one or more of the non-volatile silicones discussed previously. The oil phase may comprise, for example, between about 10% and about 30% of the composition by weight.

An antiperspirant product having a stripe (see FIGS. 1 and 2) can have the following composition.

| Ingredient | Weight % |
| --- | --- |
| Outer portion: | |
| Volatile silicone (D4)[1] | 38.59 |
| EAZCH powder | 24.00[2] |
| Silica (R972)[3] | 0.72 |
| Silica (300)[3] | 0.18 |
| Stearyl alcohol | 20.00 |
| MP70 Castor wax[4] | 2.84 |
| Myristyl myristate | 1.92 |
| PPG-14 Butyl ether | 11.00 |
| Fragrance-1539[5] | 0.75 |
| Stripe portion: | |
| Volatile silicone (D4) | 37.49 |
| EAZCH powder | 19.00[6] |
| Silica (R972) | 0.72 |
| Silica (300) | 0.18 |
| Stearyl alcohol | 20.00 |
| MP70 Caster wax | 2.84 |
| Myristyl myristate | 1.92 |
| PPG-14 Butyl ether | 11.00 |
| Colorona Dark Blue[7] | 0.10 |
| Fragrance-1539 | 0.75 |
| InCap 1539[8] | 6.00 |

[1]Dow Chemical (DC 245 fluid).
[2]USP wt. % = 18.3%.
[3]Degussa Corporation.
[4]Modified castor oil purchased from CashChem.
[5]Fragrance purchased from Haarmann and Reimer.
[6]USP wt. % = 14.5%.
[7]Pigment/colorant, purchased from Rona, division of EM Chemicals.
[8]Encapsulated fragrance purchased from Haarmann and Reimer.

Referring to FIGS. 3a–3e, an antiperspirant product including the above composition can be prepared by inserting a hollow template 24 into inverted container 12. Hollow section 26 of template is filled with the stripe composition in molten form. After the blue composition has solidified template 24 is removed and the remaining space in the container filled with the outer composition in molten form.

Antiperspirant product 10 can also be prepared by modifying the procedures described in U.S. Ser. No. 09/784,488, U.S. Ser. No. 09/784,487, and/or U.S. Ser. No. 09/784,493, all of which were filed on Feb. 15, 2001, have the same owner as the present application, and are hereby incorporated by reference. "Optically clear" as used herein, is defined in these applications. Other examples of antiperspirant compositions and striped portions that can be used in product 10 (with appropriate modification) are described in U.S. Ser. No. 09/784,488.

Figure 4A:
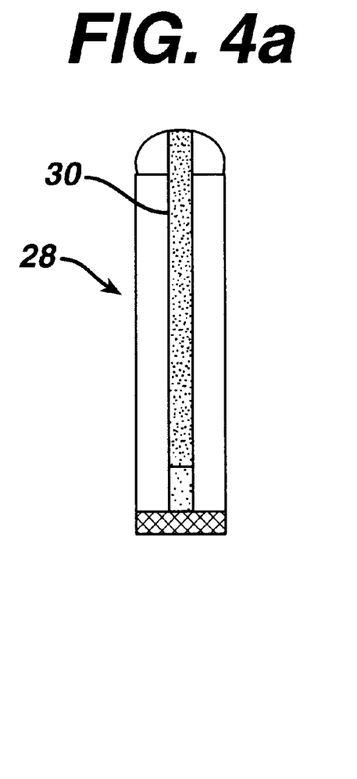
FIGS. 4a–4d are side views of an alternative product including a stripe.
Figure 4B:
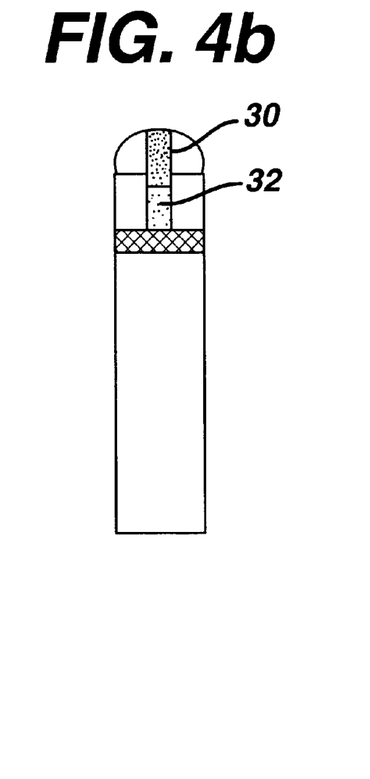
Figure 4C:
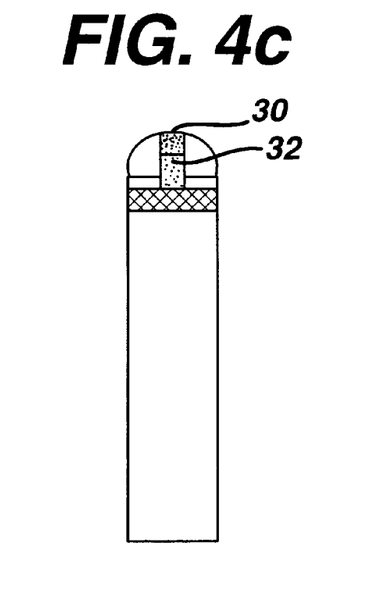
Figure 4D:
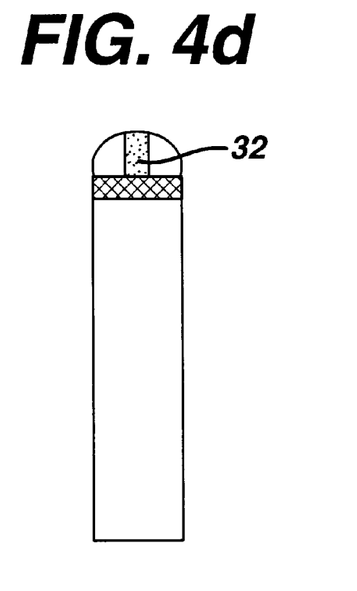
Figure 5A:
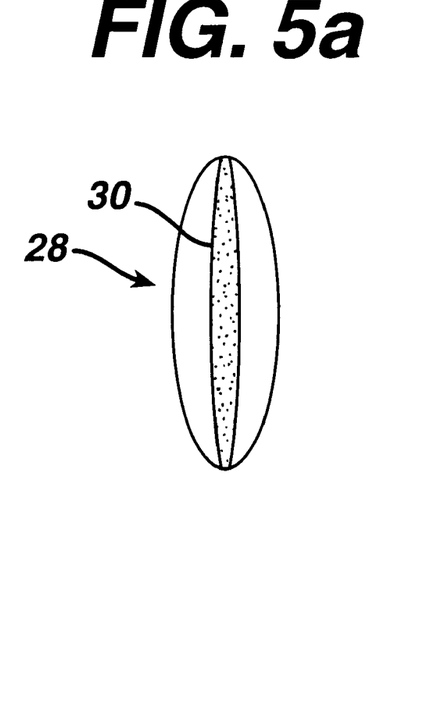
FIGS. 5a–5d are top views of the product in FIGS. 4a–4e respectively.
Figure 5B:
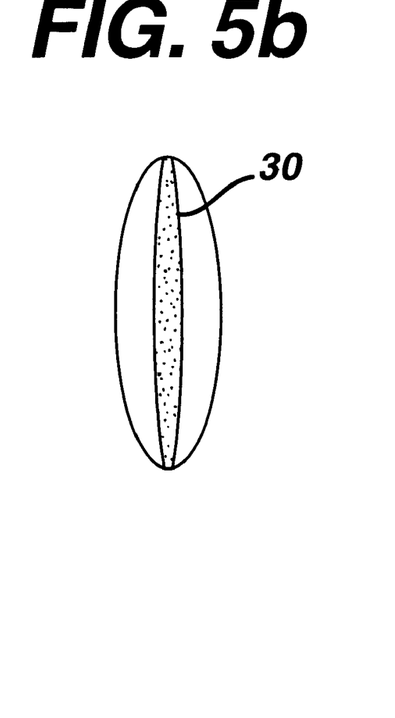
Figure 5C:
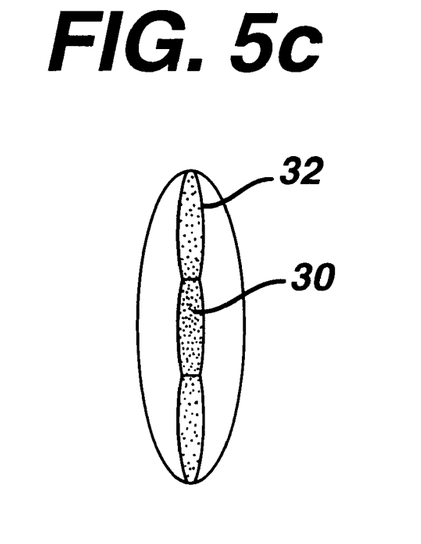
Figure 5D:
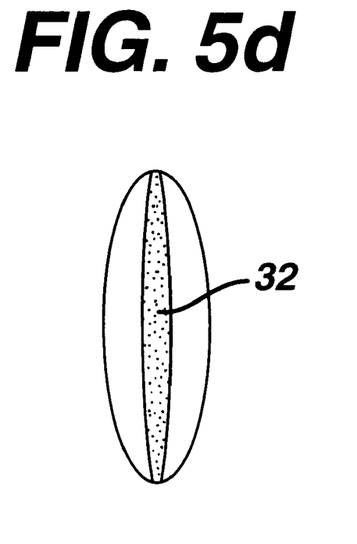
Figure 6A:
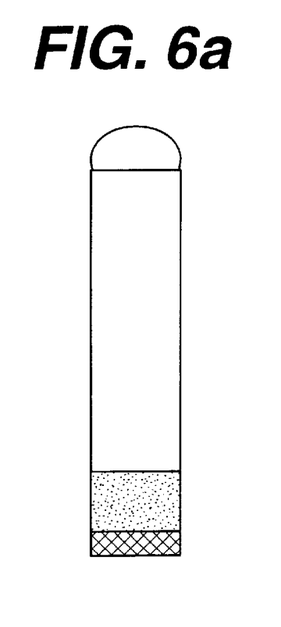
FIGS. 6a–6e are side views of an alternative product.
Figure 6B:
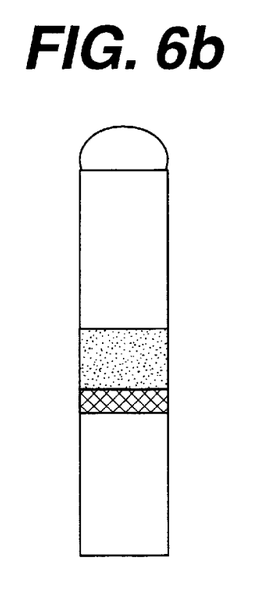
Figure 6C:
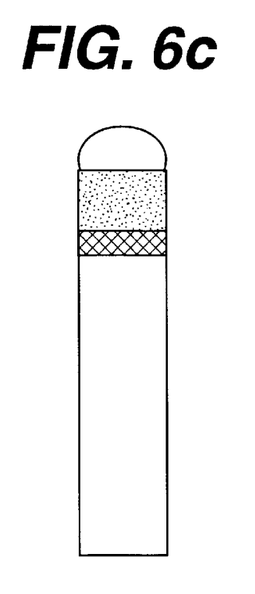
Figure 6D:
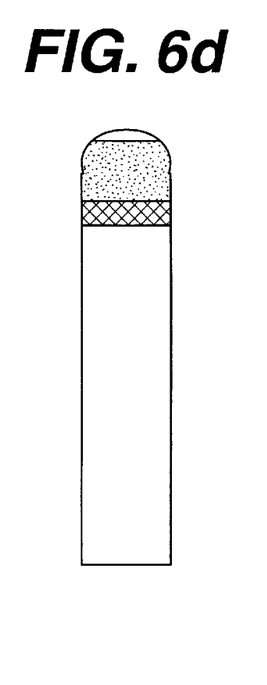
Figure 6E:
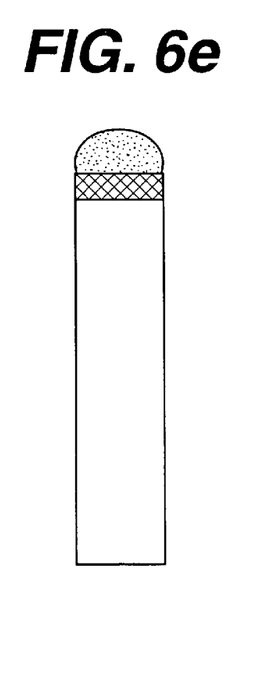
Figure 7A:
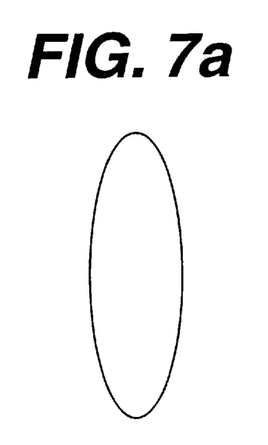
FIGS. 7a–7e are top views of the product in FIGS. 6a–6e, respectively.
Figure 7B:
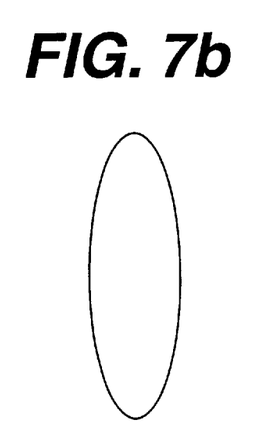
Figure 7C:
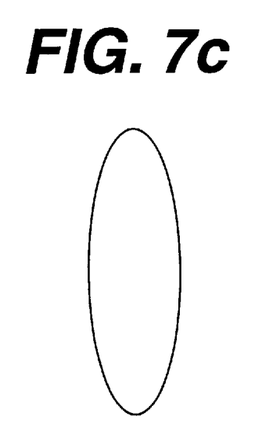
Figure 7D:
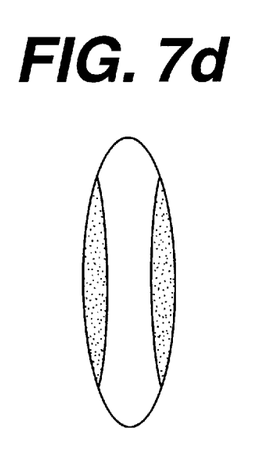
Figure 7E:
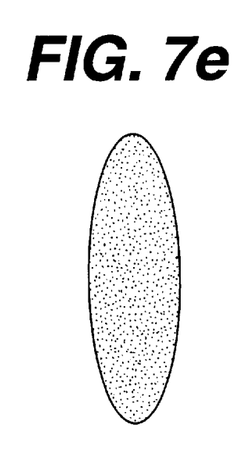
Figure 8A:
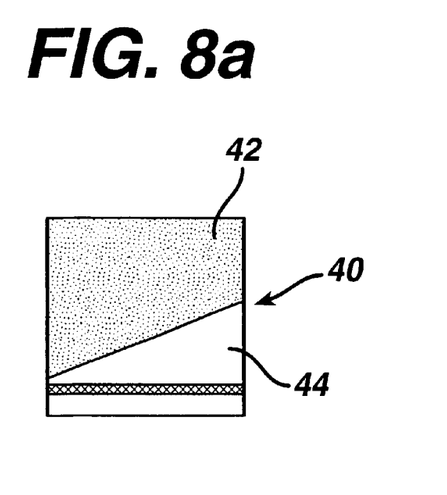
FIGS. 8a–8d are side views of an alternative product.
Figure 8B:
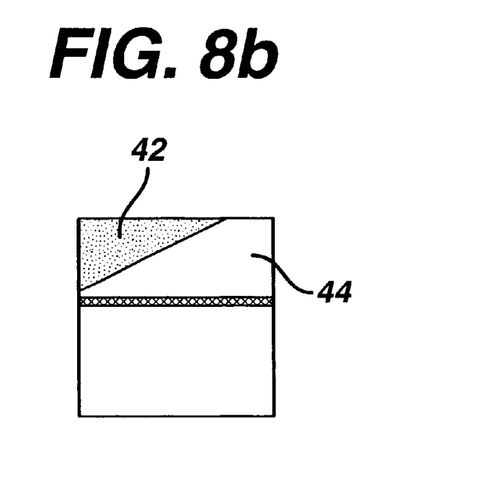
Figure 8C:
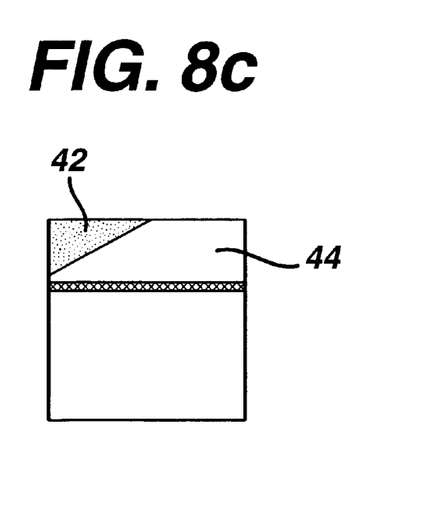
Figure 8D:
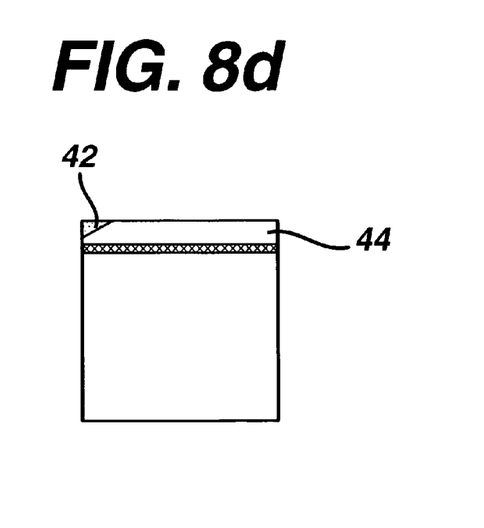
Figure 9A:
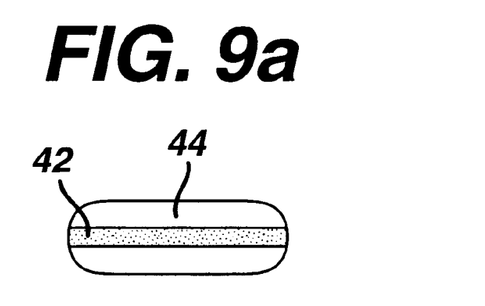
FIGS. 9a–9d are top views of the product in FIGS. 8a–8d, respectively.
Figure 9B:
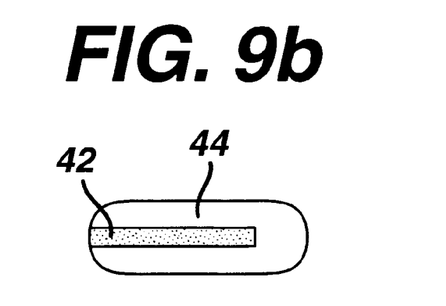
Figure 9C:
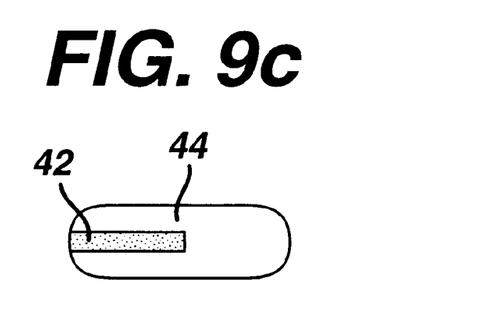
Figure 9D:
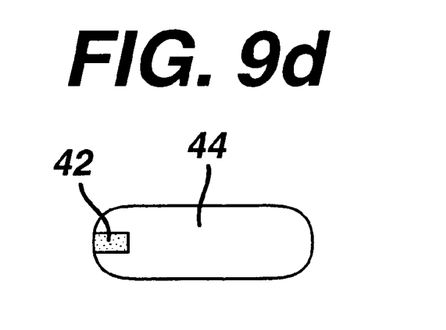
Figure 10A:
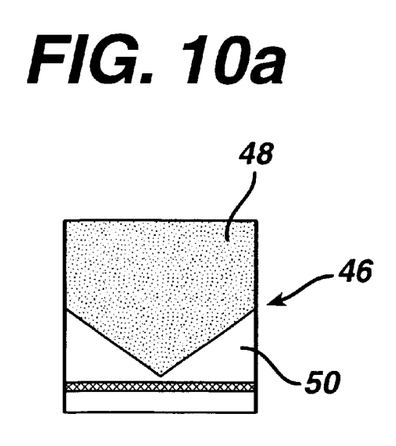
FIGS. 10a–10d are side views of an alternative product.
Figure 10B:
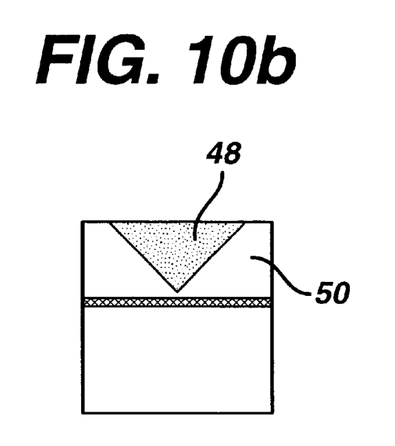
Figure 10C:
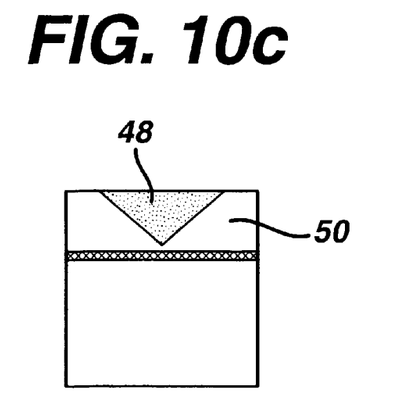
Figure 10D:
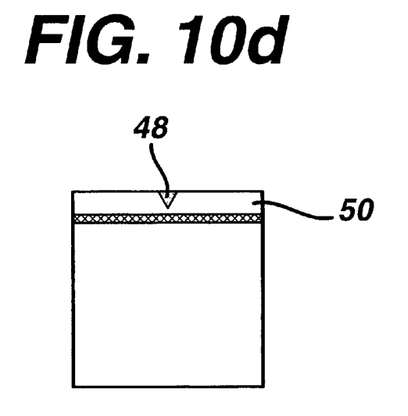
Figure 11A:
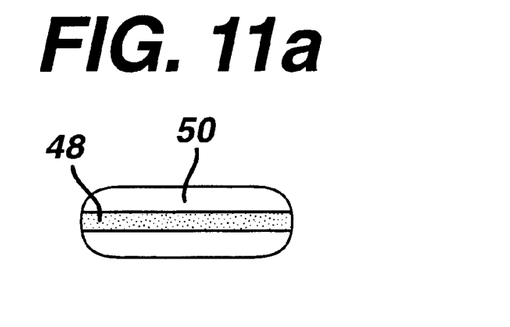
FIGS. 11a–11d are top views of the product in FIGS. 10a–10d, respectively.
Figure 11B:
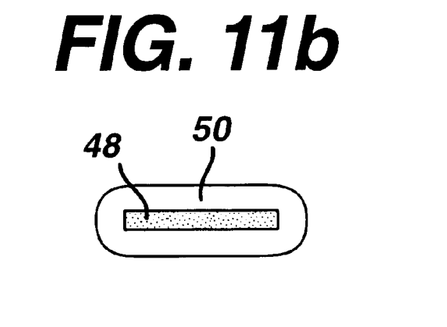
Figure 11C:
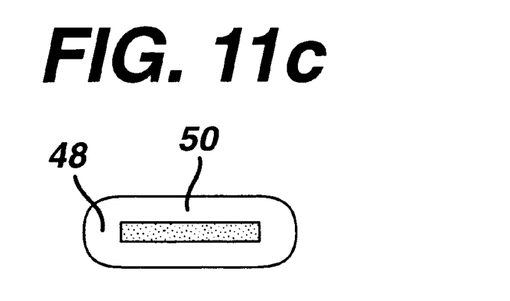
Figure 11D:
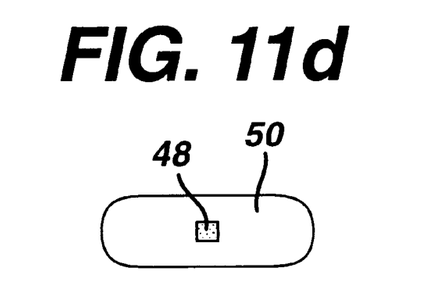

Referring to FIGS. 4a and 5a, alternative product 28 includes striped portions 30 and 32. Striped portion 30 is positioned like stripe portion 20 (previously described) and extends about 90% of the distance from the application surface to the lower end of the composition. Striped portion 32, which has a different color than striped portion 30, extends from the bottom end of striped portion 30 to the lower end of the composition.

Referring to FIGS. 4b–4d and 5b–5d, as product 28 is used the bottom end of striped portion 30 moves closer to the application surface. Eventually, the bottom end reaches the application surface and striped portion 32 begins to become exposed. As a result, the application surface changes in appearance and provides the user with a visual indication that product 28 has largely been consumed.

Other embodiments are within the claims. For example, the visual indication can be provided by a portion that appears for the first time towards the lower end of the composition. For example, the composition may include two thin lines parallel to, and on either side of, a central stripe. The central stripe can extend from the application end to the lower end of the composition, but the parallel lines may extend only a short distance upward from the lower end. Alternatively, the composition may include the thin parallel lines, but no central stripe.

The change in appearance of the composition can be provided by a variety of patterns in addition to a stripe or thin line. The change in appearance can be provided, for example, by a swirl or marbled pattern, or by the inclusion of geometric shapes such as beads, stars, diamonds, etc. The pattern may result, for example, from one portion being optically clear and the other portion being opaque.

Referring to FIGS. 6 and 7, an alternative product 34 includes a composition including upper portion 36 and lower portion 38, which has a different color than upper portion 36. As product 34 is used, bottom portion 36 moves closer to the application surface and eventually becomes exposed. As a result, the application surface changes in appearance and provides the user with a visual indication the product has largely been consumed. The upper portion of product 34 also can be provided with a central stripe having the same color as the lower portion.

Referring to FIGS. 8–11, alternative products 40 and 46 include upper portions 42 and 48, respectively, and lower portions 44 and 50 respectively. The upper and lower portions each have a colored stripe section, but the lateral length of the colored stripe section is different in the lower portion than in the upper portion. The application surface of composition 40 and 46 initially each include a central stripe that extends across the entire lateral length, but then after about 70% of the composition has been consumed the stripe gradually and continuously diminishes in lateral length and eventually disappears. In product 40, the stripe regressively disappears from one side to the other side (much like a fuel gauge), while in product 46 the stripe regressively disappears from both edges toward the middle.

In the foregoing description, where the product is referred to as an antiperspirant product, it should be understood that the product may be another type of cosmetic or therapeutic product, such as for example a deodorant product. The composition may be a deodorant composition including two portions or a combined antiperspirant/deodorant composition in which one portion includes an effective amount of a deodorant active ingredient and the other portion includes an antiperspirant salt. Moreover, the composition may include three, four, or even five portions.

What is claimed is:

1. A product for application to skin, comprising
   a container having an open end, and
   a non-flowable composition within the container having an application surface at the open end of the container and including a cosmetic or therapeutic active ingredient, the application surface continuously wearing away during application of the composition to the skin, the application surface prior to first use of the product having a first visual appearance and the application surface at some time after the first use having a second visual appearance, different from any prior visual appearance of the application surface, caused by a change in the composition, wherein the second visual appearance provides an indication that the end of the composition is near.

2. The product of claim 1, wherein the active ingredient comprises an antiperspirant salt.

3. The product of claim 2, wherein the composition comprises from 2 USP weight percent to 25 USP weight percent of an antiperspirant salt.

4. The product of claim 3, wherein the antiperspirant salt is an aluminum or aluminum/zirconium salt.

5. The product of claim 1, wherein the active ingredient comprises a deodorant active ingredient.

6. The product of claim 1, wherein the active ingredient comprises a skin treatment component selected from the group consisting of sunscreen, vitamin E, alphahydroxy acids, or a fragrance.

7. The product of claim 1, wherein the active ingredient comprises a pharmaceutical active or a therapeutic active.

8. The product of claim 1, wherein the container includes a platform in contact with a lower end of the composition.

9. The product of claim 1, wherein the change in the composition comprises a color change affecting at least part of the application surface.

10. The product of claim 1, wherein the change in the composition comprises a change in a pattern on the application surface.

11. The product of claim 10, wherein the change in the pattern comprises a disappearance of a stripe on the application surface.

12. The product of claim 10, wherein the change in the pattern comprises an appearance of a stripe on the application surface.

13. The product of claim 10, wherein the change in the pattern comprises new color for all or part of the application surface.

14. The product of claim 1, wherein the visual appearance of the application surface continuously changes with use of the product for a period of time during consumption of the composition.

15. The product of claim 1, wherein the first visual appearance and/or the second visual appearance is selected from the group consisting of stripes, swirls, and marbled appearances.

16. The product of claim 1, wherein the second visual appearance occurs after at least about 80% of the composition has been consumed.

17. The product of claim 1, wherein prior to first use the composition includes a stripe extending approximately from one side of the composition to a second side of the composition across the application surface, the stripe having a different color than the adjacent application surface.

18. The product of claim 17, wherein the stripe extends only partially height-wise through the composition.

19. A product for application to the skin, comprising
   a container having an open end and a platform disposed within the container and adapted to move toward the open end; and
   a non-flowable composition within the container extending from the platform toward the open end, the composition including a cosmetic or therapeutic active ingredient, wherein the outermost portion of the composition which is exposed at the open end of the container provides an application surface for rubbing the composition against the skin, the application surface continuously wearing away with use, the composition having an upper portion toward the open end of said container and a lower portion at least about 70% toward the internal platform, wherein the lower portion has a different composition than the upper portion such that when said lower portion becomes exposed at the open end upon use, it provides a different visual appearance at the application surface than the upper portion.

20. A product for underarm application, comprising
   an opaque container having an open end,
   a non-flowable composition within the container including an antiperspirant salt and/or deodorant active ingredient and having an application surface at the open end of the container, and
   a usage indicator within the container that provides a visual indication that at least 70% of the composition has been consumed.

21. A product for application to the skin, comprising
   a container having an open end
   a non-flowable composition within the container including a cosmetic or therapeutic active ingredient, the composition having a height defined by an application surface at the open end and a lower end, the composition farther including a stripe extending downwards from the application surface, the composition further including a thin line parallel to the stripe extending upwards from the lower end of the composition.

22. A product for application to skin, comprising
   a container having an open end, and
   a non-flowable composition within the container having an application surface at the open end of the container and including a cosmetic or therapeutic active ingredient, the application surface continuously wearing away during application of the composition to the skin, the application surface prior to first use of the product having a first visual appearance and the application surface at some time after the first use having a second visual appearance caused by a change in the composition, wherein the change in the pattern comprises a disappearance of a stripe on the application surface.

23. A product for application to skin, comprising
   a container having an open end, and
   a non-flowable composition within the container having an application surface at the open end of the container and including a cosmetic or therapeutic active ingredient, the application surface continuously wearing away during application of the composition to the skin, the application surface prior to first use of the product having a first visual appearance and the application surface at some time after the first use having a second visual appearance caused by a change in the composition, wherein the change in the pattern comprises an appearance of a stripe on the application surface.

24. A product for application to skin, comprising a container having an open end, and a non-flowable composition within the container having an application surface at the open end of the container and including a cosmetic or therapeutic active ingredient, the application surface continuously wearing away during application of the composition to the skin, the application surface prior to first use of the product having a first visual appearance and the application surface at some time after the first use having a second visual appearance caused by a change in the color of a portion of the composition at a specific height in the composition, wherein the visual appearance of the application surface continuously changes with use of the product for a period of time during consumption of the composition.

25. A product for application to skin, comprising a container having an open end, and a non-flowable composition within the container having an application surface at the open end of the container and including a cosmetic or therapeutic active ingredient, the application surface continuously wearing away during application of the composition to the skin, the application surface prior to first use of the product having a first visual appearance and the application surface at some time after the first use having a second visual appearance caused by a change in the composition, wherein prior to first use the composition includes a stripe extending approximately from one side of the composition to a second side of the composition across the application surface, the stripe having a different color than the adjacent application surface.

26. The product of claim 25, wherein the stripe extends only partially height-wise through the composition.

* * * * *

UNITED STATES PATENT AND TRADEMARK OFFICE
CERTIFICATE OF CORRECTION

PATENT NO.    : 6,506,369 B1
DATED         : January 14, 2003
INVENTOR(S)   : Michael J. Moloney et al.

It is certified that error appears in the above-identified patent and that said Letters Patent is hereby corrected as shown below:

Column 10,
Line 44, delete "farther" and replace with -- further --.

Signed and Sealed this

Twenty-second Day of April, 2003

JAMES E. ROGAN
*Director of the United States Patent and Trademark Office*